United States Patent
Zacharias (12)

(10) Patent No.: US 6,939,317 B2
(45) Date of Patent: Sep. 6, 2005

(54) REPETITIVE PROGRESSIVE AXIAL DISPLACEMENT PATTERN FOR PHACOEMULSIFIER NEEDLE TIP

(76) Inventor: Jaime Zacharias, Av Luis Pasteur 5917, Vitacura, Santiago (CL)

( * ) Notice: Subject to any disclaimer, the term of this patent is extended or adjusted under 35 U.S.C. 154(b) by 0 days.

(21) Appl. No.: 10/710,888

(22) Filed: Aug. 10, 2004

(65) Prior Publication Data

US 2005/0096680 A1    May 5, 2005

Related U.S. Application Data

(60) Provisional application No. 60/481,204, filed on Aug. 10, 2003.

(51) Int. Cl.$^7$ .......................... A61B 17/20; A61B 17/32; A61F 9/00
(52) U.S. Cl. .......................... 604/22; 606/107; 606/169
(58) Field of Search .............................. 604/20–22, 19, 604/294; 606/107, 169; 623/6.12; 601/2, 601/46, 48, 87, 93, 101

(56) References Cited

U.S. PATENT DOCUMENTS

| | | | | |
|---|---|---|---|---|
| 5,733,256 A | * | 3/1998 | Costin | 604/22 |
| 5,808,396 A | * | 9/1998 | Boukhny | 310/318 |
| 5,843,109 A | * | 12/1998 | Mehta et al. | 606/169 |
| 6,402,769 B1 | * | 6/2002 | Boukhny | 606/169 |
| 2002/0193817 A1 | * | 12/2002 | Lal et al. | 606/169 |

* cited by examiner

*Primary Examiner*—Nicholas D. Lucchesi
*Assistant Examiner*—Sundeep Virdi

(57) ABSTRACT

A method to improve phacoemulsification efficiency by providing bursts of axial ultrasonic activity in synchronization with a fraction of a lower frequency axial oscillatory activity, the fraction corresponding to the portion of the low frequency signal that displaces toward the lens fragments and distally from the phacoemulsification hand-piece. Ultrasonic bursts synchronized with displacement of the phacoemulsification needle tip toward the lens tissue increases efficiency allowing the reduction of the required ultrasonic power minimizing heat generation and cavitation.

1 Claim, 9 Drawing Sheets

A

B

C

REPETITIVE PROGRESSIVE AXIAL DISPLACEMENT PATTERN FOR PHACOEMULSIFIER NEEDLE TIP

BACKGROUND OF INVENTION

1. Field of Invention

This invention is related to motion control of a tissue emulsifier needle and more particularly to the axial displacement pattern followed by the tip of an emulsifier needle used to emulsify biological tissues such as the phacoemulsification of the crystalline lens during eye surgery.

2. Description of Prior Art

Current phacoemulsification apparatus usually use electro-mechanic actuators driven at sonic or ultrasonic frequencies to energize a hollow phacoemulsification needle. These actuators operate under piezoelectric, magnetostrictive or voice-coil principles.

Axial sinusoidal oscillation of the phacoemulsification needle emulsifies the lens tissue of the eye during cataract surgery primarily by jackhammer action. Friction between the hollow phacoemulsification needle external walls and the surrounding elements generates undesired heat that can lead to thermal injury of the ocular tissues. Also high intensity ultrasonic activity produces undesired cavitation bubbles.

Several measures have been adopted to minimize the risk of thermal injury. For example, it is a necessary condition that cooling fluid circulates before ultrasonic power can be applied in order to guarantee sufficient heat dissipation. Also, an aspiration bypass port, consisting in a lateral shunt located near the distal opening has been added to refrigerate the surroundings of the phacoemulsification needle when the distal opening of the phacoemulsification needle becomes occluded by lens material.

Furthermore, various schemes of modulation of the driving signal that powers the ultrasonic electro-mechanic actuators have been used to reduce the thermal risk during the procedure. These schemes consider the intercalation of periods of actuator inactivity that provide thermal relaxation before the following period of ultrasonic oscillatory activity takes place, minimizing heat build up.

In this direction, Pulsed Mode is one of the basic power modulation schemes typically having a 50% duty cycle where a burst of ultrasonic activity is followed by an equal period of inactivity, usually providing up to 15 pulses per second.

Burst Mode is another scheme that provides an energized actuator for a fixed predetermined period, typically above 30 milliseconds duration, followed by an operator controlled period of actuator inactivity and repeated in cycles.

Recently, systems providing very short bursts in the order of 4 milliseconds have been introduced, with a user selectable separation between bursts. This method has been claimed to generate less heat and to provide more lens disruption power for similar ultrasound energy levels delivered into the ocular tissues. The explanation raised for the increased efficiency produced by this mode would consist in a relative increase of transient cavitation over steady cavitation.

Inventor's research on phacoemulsification needle interaction with lens tissue using high speed recording techniques has revealed that the most efficient portion of an ultrasonic burst to disrupt lens tissue occurs when the amplitude of oscillations increases at the initial portion of each single burst. This portion of a burst can be defined as the attack portion of the envelope of the motion burst.

Once the amplitude of oscillations attains the maximum preset steady amplitude, efficiency to disrupt tissue decreases to an intermediate level, as observed by the speed at which a fragment of cataract tissue advances into the phacoemulsification needle tip.

The same studies teach that during ultrasonic activity only a small portion of the tip axial excursion located at the distal end of each stroke has real contact with the lens tissue being emulsified. This occurs because the high repetition rate of each stroke does not allow a lens fragment to follow the full trajectory of the phacoemulsification needle because of fragment inertia.

The lens fragment remains at the distal zone of the excursion of the phacoemulsification needle tip during steady ultrasound. Only about 5 degrees of the sinusoidal trajectory located before the apex of the stroke of the phacoemulsification needle tip enters in contact with the lens fragment during steady ultrasonic activity.

This situation is different during the attack and decay portions of a single ultrasonic burst. During the attack portion the amplitude of ultrasonic oscillations progressively increases. Lens fragment inertia during the attack portion allows the phacoemulsification needle tip to produce a relatively higher lens disruptive effect when compared to the steady ultrasound lens disruptive effect.

In the opposite way, during the decay or ending portion of a single burst of ultrasonic activity, the lens disruptive effect is greatly reduced with respect to the ultrasound lens disruptive effect observed during steady ultrasound because contact between the needle tip and the lens fragment is diminished.

Object and Advantages. A main object of the present invention is to provide a method to increase the efficiency of phacoemulsification needles with respect to currently used methods of ultrasonic energy delivery for lens removal, allowing the effective use of less ultrasonic power and decreasing heat generation.

A further object of the present invention is to reduce the delivery of ultrasonic energy into the eye during the periods of ultrasonic activity known to provide minimal or no lens disruptive power.

An advantage of the present invention is to reduce the undesired thermal and cavitation effects when compared to currently used systems with similar degrees of lens removing capabilities. Further objects and advantages of the present invention will become apparent from consideration of the drawings and ensuing description.

SUMMARY OF INVENTION

A method to improve the efficiency of a phacoemulsifier system based on a novel phacoemulsification needle tip axial displacement pattern designed to increase the exposure of a lens fragment to successive strokes of ultrasonic activity of the phacoemulsification needle tip. The method also considers avoiding delivery of ultrasonic power during the periods of ultrasonic activity where minimal lens removing capabilities are known to occur.

Increased exposure of lens fragments to phacoemulsification needle tip action during each ultrasonic stroke according to the present invention is achieved by using a low frequency axial displacement carrier signal and by activating the ultrasonic energy preferably in phase with the fraction of the low frequency motion component corresponding to displacement of the tip towards the distal limit with respect to the hand-piece.

REFERENCE NUMERALS FOR FIGURES

1.—attack, 2.—steady state, 3.—decay, 10.—hand piece controller unit, 12.—connector, 14.—external control, 16.—connector, 18.—low frequency oscillator-driver unit, 20.—connector, 22.—ultrasonic oscillator-driver unit, 24.—connector, 25.—low frequency position sensor, 26.—connector, 30.—connector, 32.—phase-position detector, 34.—connector, 40.—aspiration line connector, 50.—low frequency electro-mechanic transducer, 52.—coupler, 56.—distal ultrasonic resonant body, 58.—proximal ultrasonic resonant body, 60.—ultrasonic electro-mechanic transducer, 70.—surgical hand-piece enclosure, 80.—phacoemulsification needle, 82.—phacoemulsification needle tip.

DETAILED DESCRIPTION

Figure 1:
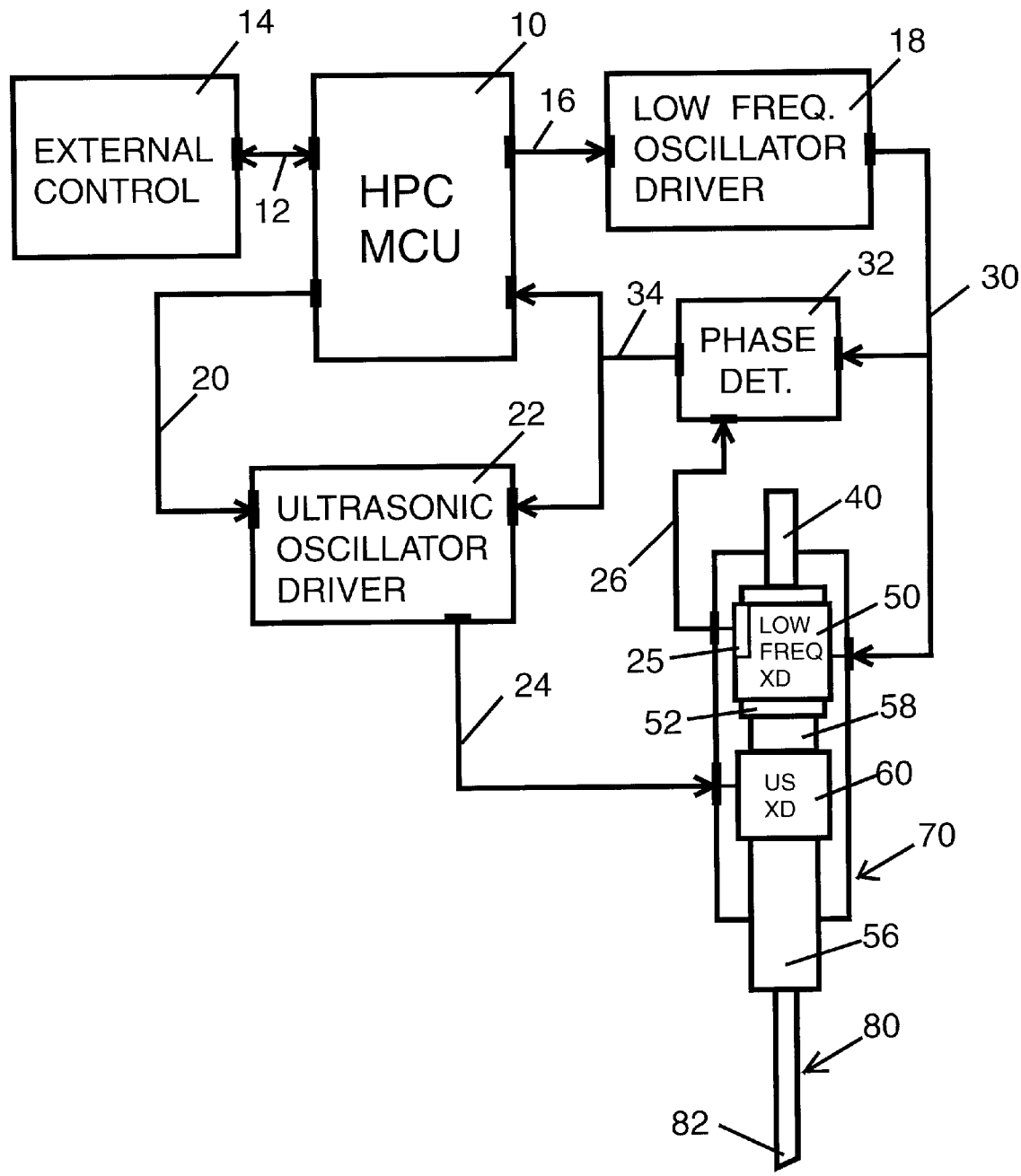
FIG. 1 depicts a block diagram of a phacoemulsification hand-piece electronic driver circuit and electro-mechanic actuators of the present invention.

As shown in FIG. 1 a hand-piece controller unit 10 interconnects through a connector 12 to a host external controller 14. Hand-piece controller unit 10 interconnects through a connector 20 to an ultrasonic oscillator driver unit 22. Hand-piece controller unit 10 interconnects through a connector 16 to a low frequency oscillator driver unit 18.

Ultrasonic oscillator driver unit 22 connects through connector 24 to an ultrasonic electro-mechanic transducer 60 located inside phacoemulsification surgical hand-piece enclosure 70. Low frequency oscillator driver 18 connects through connector 30 to a low frequency electro-mechanic transducer 50 located inside phacoemulsification surgical hand-piece enclosure 70. Low frequency oscillator driver 18 also connects through connector 30 to low frequency phase—position detector circuit 32.

Low frequency electro-mechanic transducer 50 has an attached low frequency position sensor 25 that provides a low frequency motion component phase output signal that connects through connector 26 with low frequency phase detector circuit 32. Low frequency phase detector circuit 32 connects through connector 34 with hand-piece controller unit 10 and also with ultrasonic oscillator driver unit 22.

Ultrasonic electro-mechanic transducer 60 is axially mounted between proximal resonant body 58 and distal resonant body 56. Distal resonant body 56 attaches to hollow phacoemulsification needle 80 having a needle tip 82. Low frequency electro-mechanic transducer 50 is axially coupled through coupler 52 with the proximal section of ultrasonic resonant body 58. Aspiration line connector 40 provides watertight fluid connection between an aspiration line (not shown) and the inner proximal end of hollow phacoemulsification needle 80.

Operation of the invention: A host phacoemulsifier system provides operator control and settings through external control 14. Operational parameters such as ultrasonic stroke amplitude, low frequency stroke amplitude, burst duration, burst repetition rate and activity period are provided through external control 14 that has been user configured and provides an activation signal for phacoemulsification hand-piece controller unit 10.

Hand-piece controller unit 10 configures though connector 20 ultrasonic oscillator driver 22 that in turn energizes ultrasonic electro-mechanic actuator 60 though connector 24 providing an electric signal to produce ultrasonic oscillations of a selected frequency, waveform, amplitude and duration. Typically, ultrasonic frequency will be in the range of 20.000 to 90.000 hertz according to ultrasonic oscillator driver 22 and ultrasonic electro-mechanic actuator 60 characteristics.

Hand-piece controller unit 10 also configures though connector 16 low frequency oscillator driver 18 that in turn energizes low frequency electro-mechanic actuator 50 though connector 30 providing an electric signal to produce low frequency oscillations of a selected frequency, waveform, amplitude and duration. Typically, low frequency component will be in the range of 10 to 5000 hertz according to operator settings and system construction.

Figure 2:
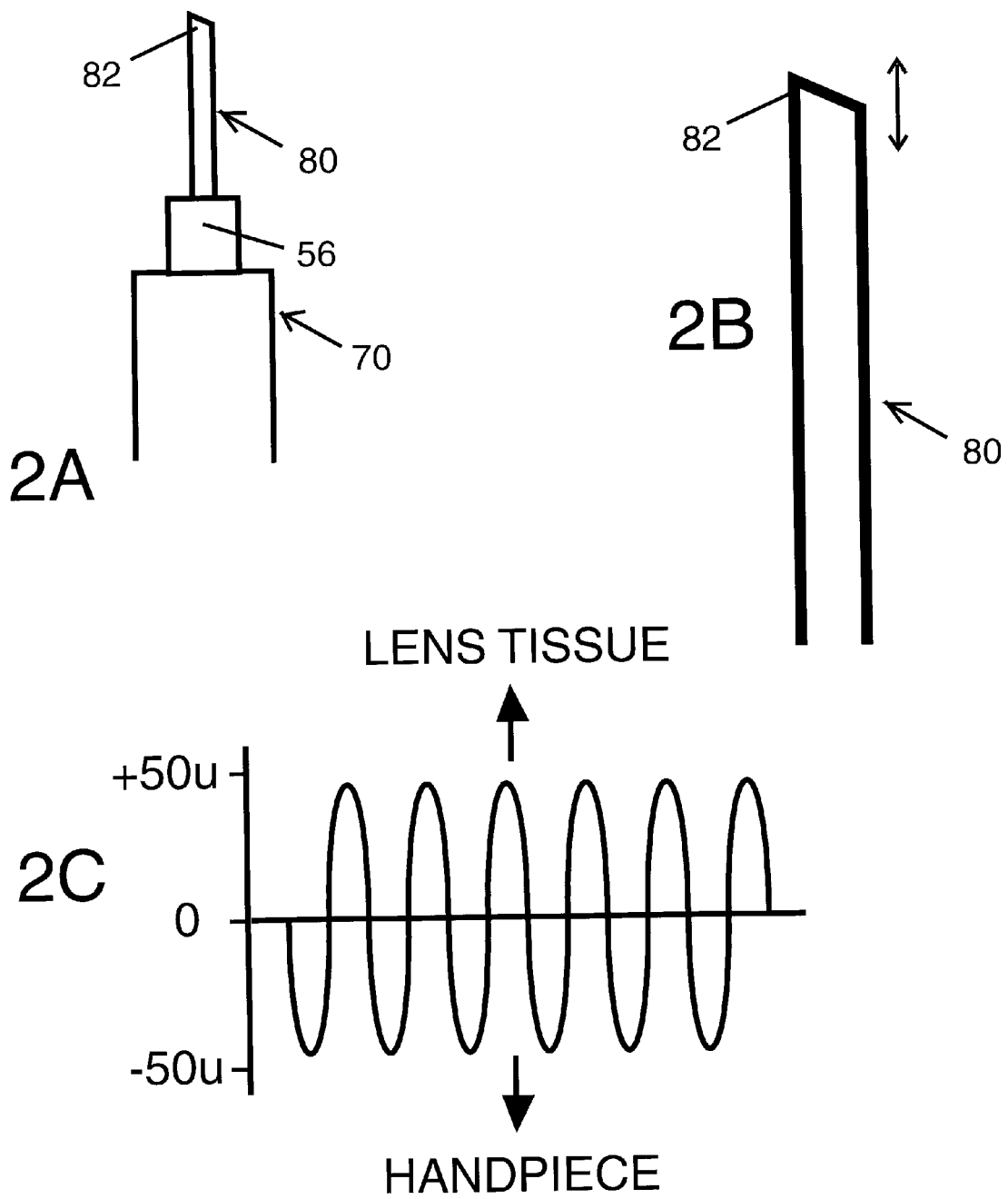
FIG. 2 depicts a longitudinal section of a phacoemulsification hand-piece and needle. A typical axial displacement pattern is illustrated.

Oscillatory activity produced by electromechanical transducers 50 and 60 axially coupled inside phacoemulsification hand-piece enclosure 70 is additively transmitted to phacoemulsification needle 80 (FIG. 2A) to produce axial displacement of the phacoemulsification needle tip 82 (FIG. 2B and FIG. 2C).

Phase-position detector 32 receives input signals from low frequency oscillator-driver 18 through connector 30 and from low frequency position sensor 25 through connector 26. Phase detector 32 produces an output signal that informs the cycle position of the low frequency component of the axial displacement of the phacoemulsifier needle tip. Phase detector 32 output signal is fed into hand-piece controller unit 10 and into ultrasonic oscillator-driver unit 22.

The ultrasonic component of the axial oscillatory displacement of phacoemulsification needle tip 82 produced by ultrasonic electro-mechanic transducer 60 can be typically regulated between 0 and 100 microns tip stroke corresponding to a phacoemulsification power range between 0 and 100% of a typical prior art system.

The low frequency component of the axial oscillatory displacement of the phacoemulsification needle tip 82 produced by low frequency electro-mechanic transducer 50 can be typically regulated between 0 and 500 microns. Both ultrasonic and low frequency components of phacoemulsification needle tip motion cycles can independently depart from a sinusoidal wave displacement pattern according to driving signal characteristics.

Tip motion versus time plots depicted in FIGS. 3, 4, 5, 6, 7, 8 and 9 depict time in the horizontal axis. Phacoemulsification needle tip position is shown in the vertical axis in all referred figures. Top of page represents distal from the phacoemulsification hand-piece and near to lens fragments position. Bottom of page represents proximal to the hand-piece in all referred figures.

Figure 3:
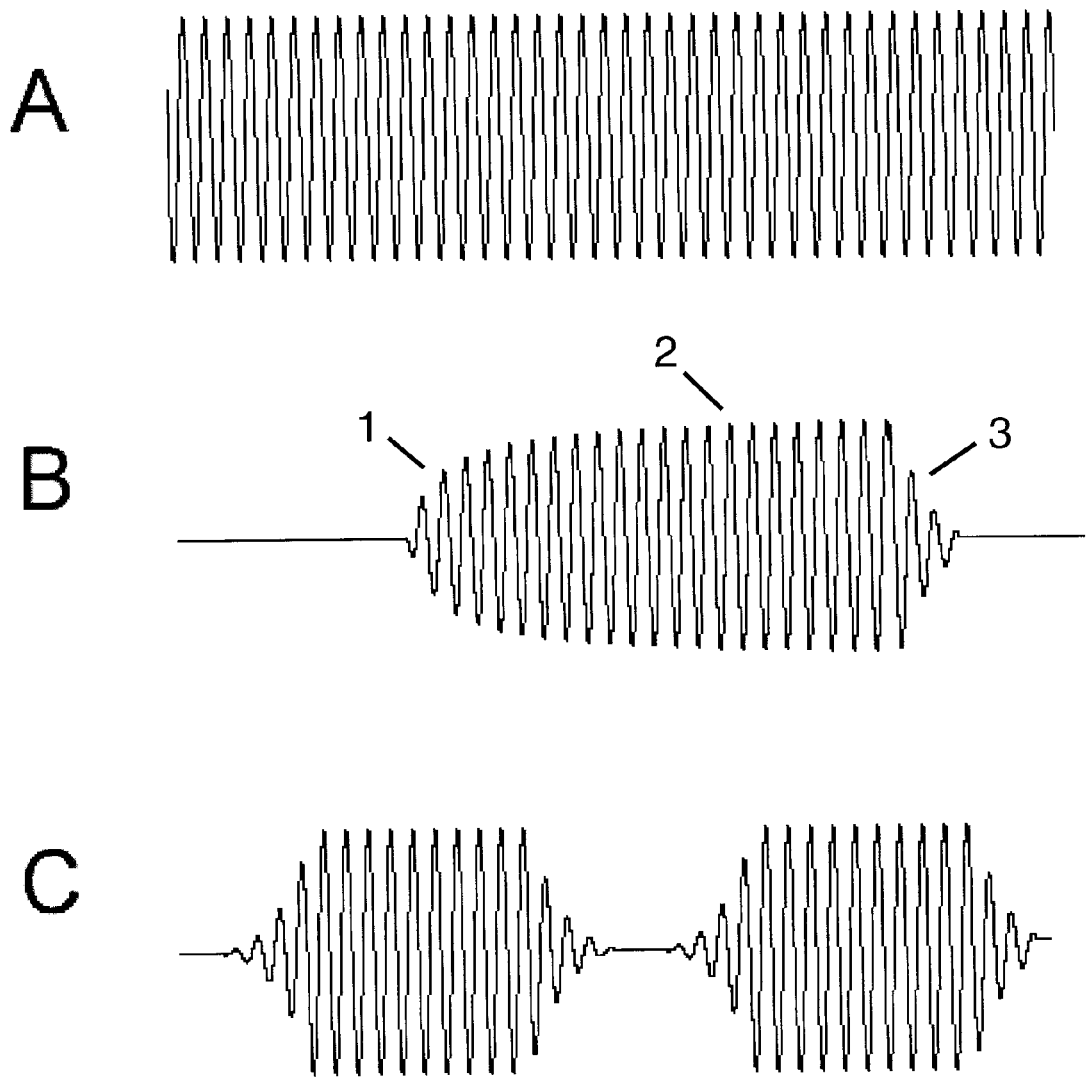
FIG. 3 depicts typical time versus displacement plots of the tip of a phacoemulsification needle using prior art methods.
Figure 4:
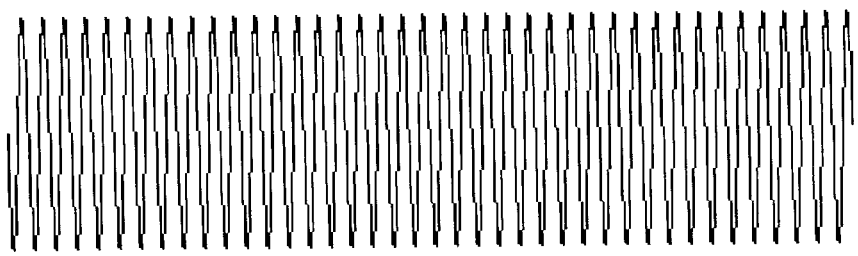
FIG. 4 illustrates one embodiment of an axial displacement pattern for a phacoemulsification tip of the present invention.
Figure 4:
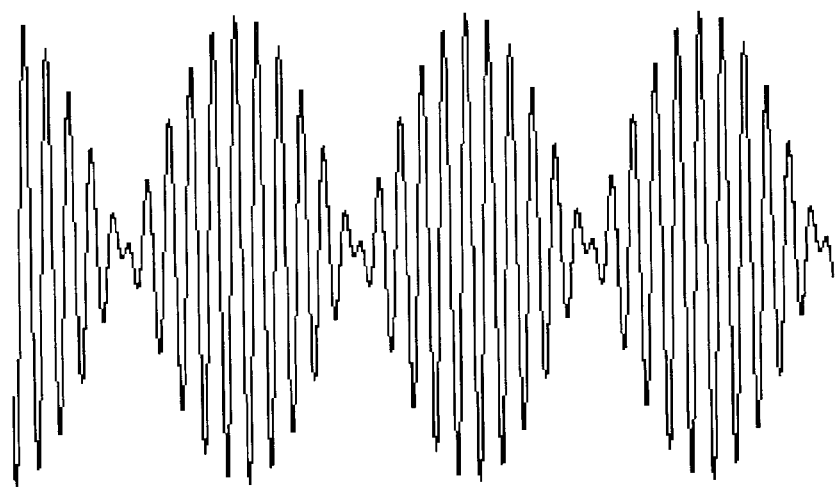
Figure 4:
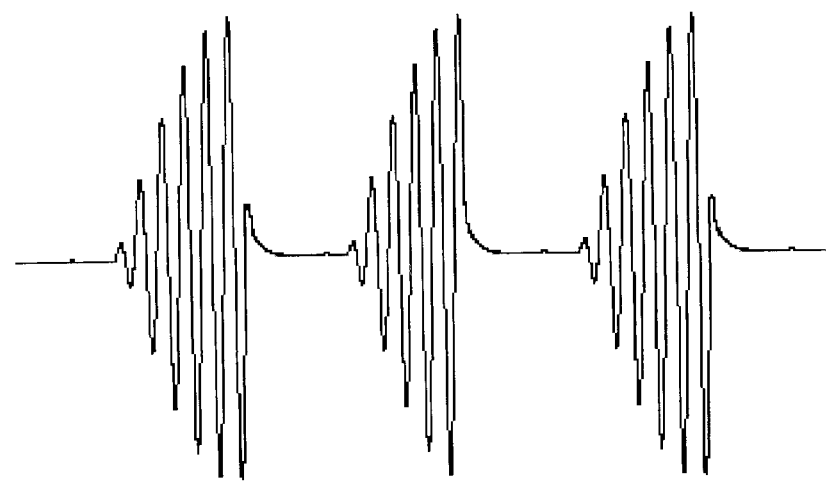
Figure 5:
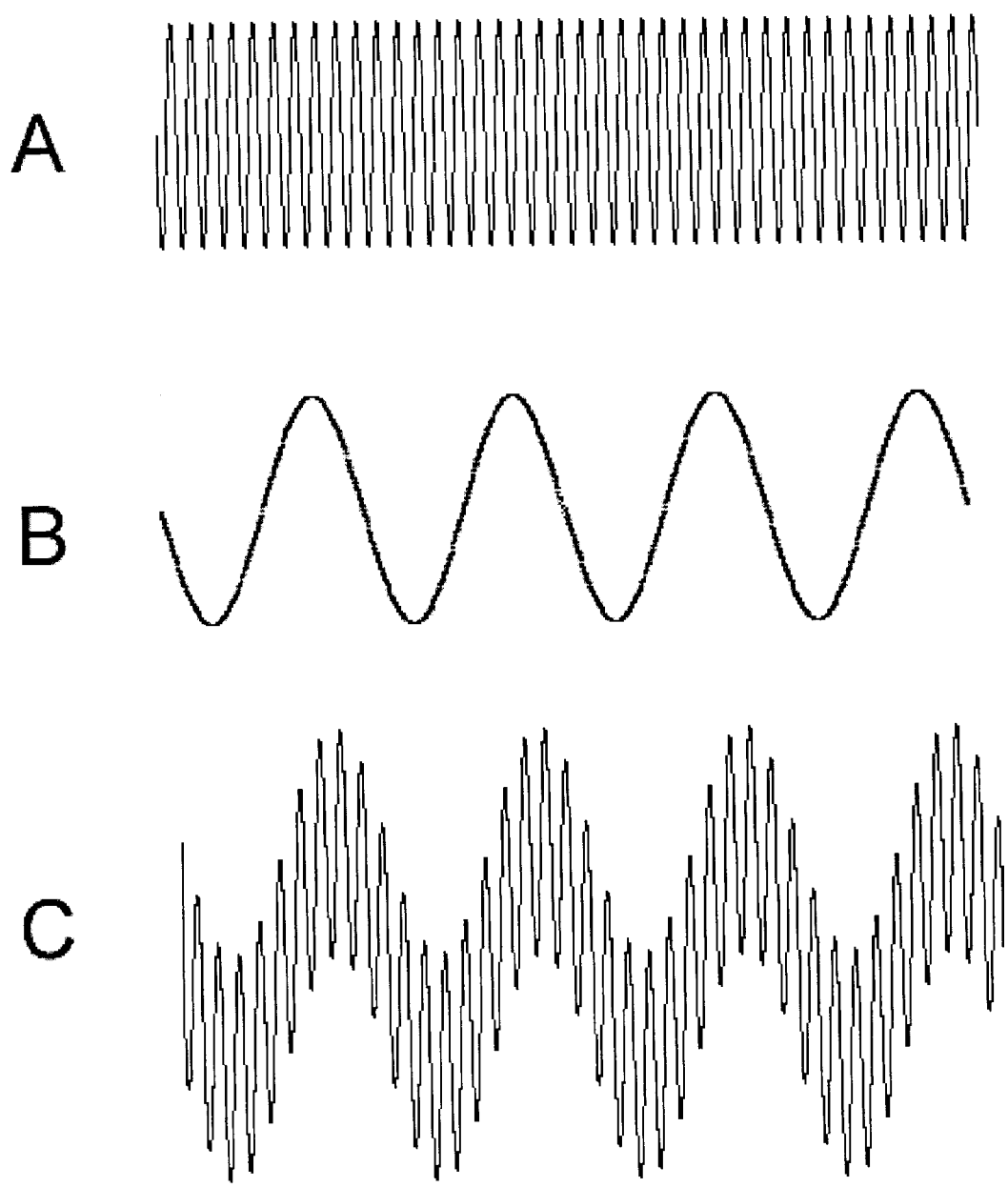
FIG. 5 illustrates one embodiment of an axial displacement pattern for a phacoemulsification tip of the present invention.
Figure 6:
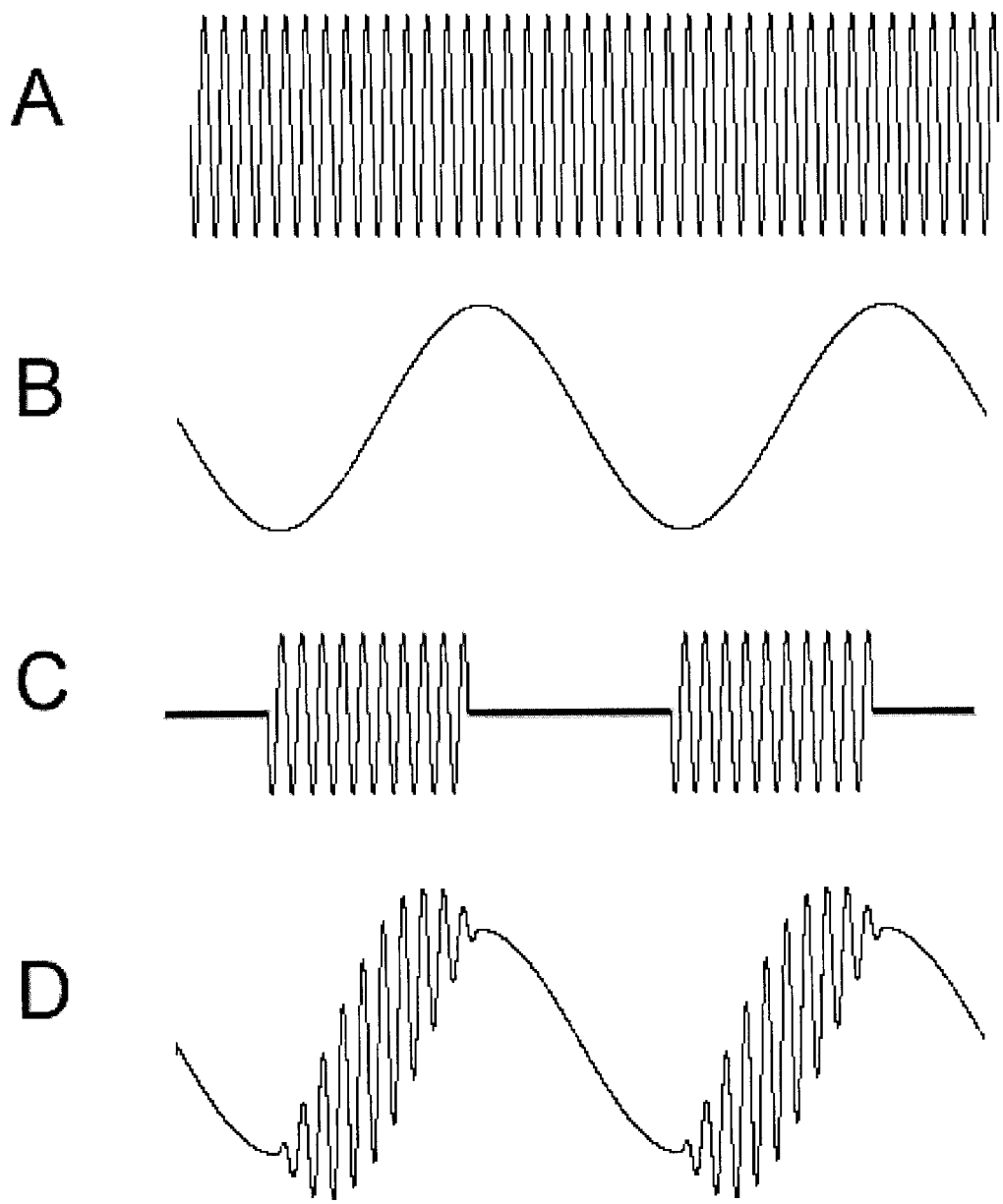
FIG. 6 illustrates a preferred embodiment of an axial displacement pattern for a phacoemulsification tip of the present invention.
Figure 7:
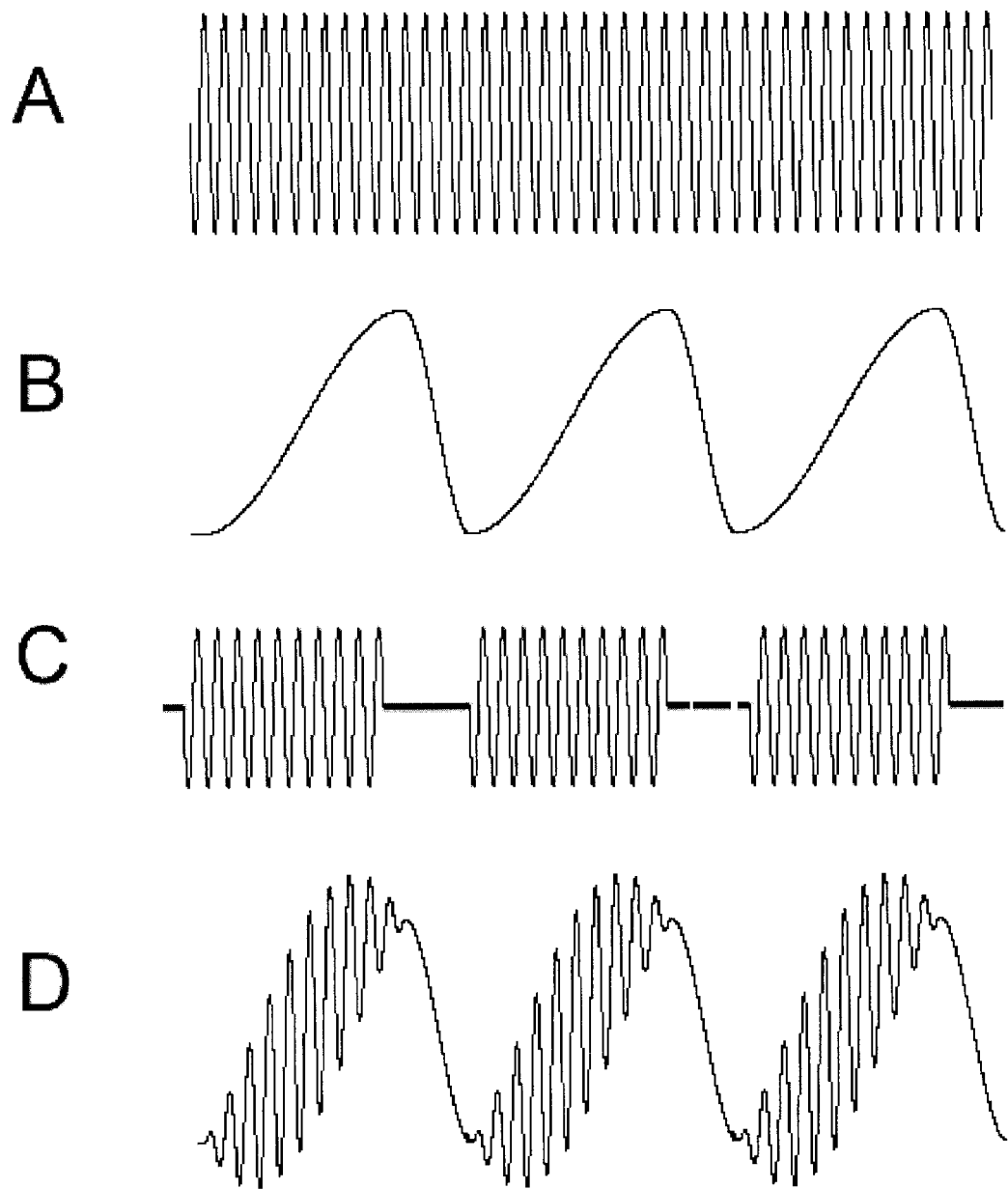
FIG. 7 illustrates another preferred embodiment of an axial displacement pattern for a phacoemulsification tip of the present invention.
Figure 8:
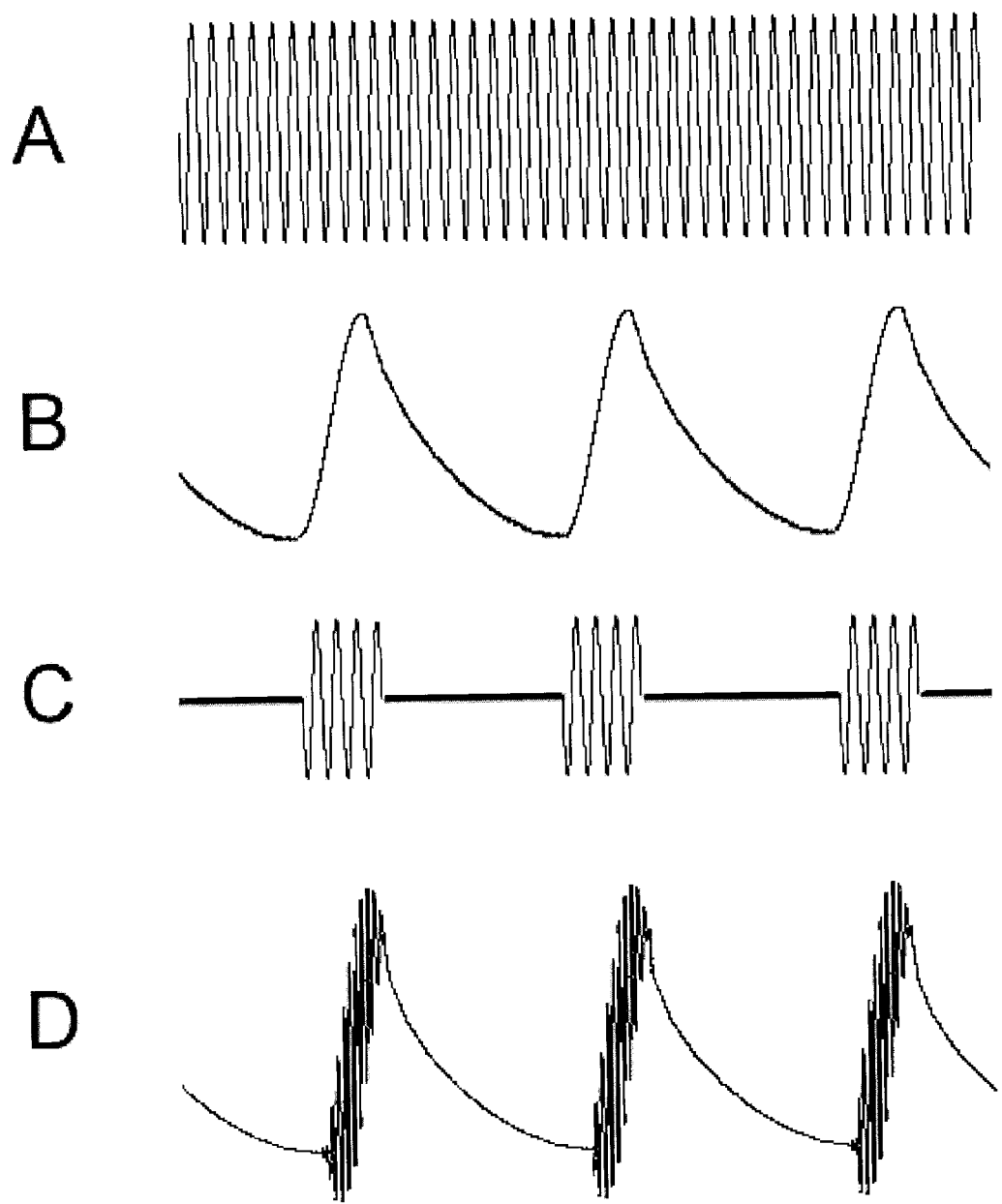
FIG. 8 illustrates another preferred embodiment of an axial displacement pattern for a phacoemulsification tip of the present invention.
Figure 9:
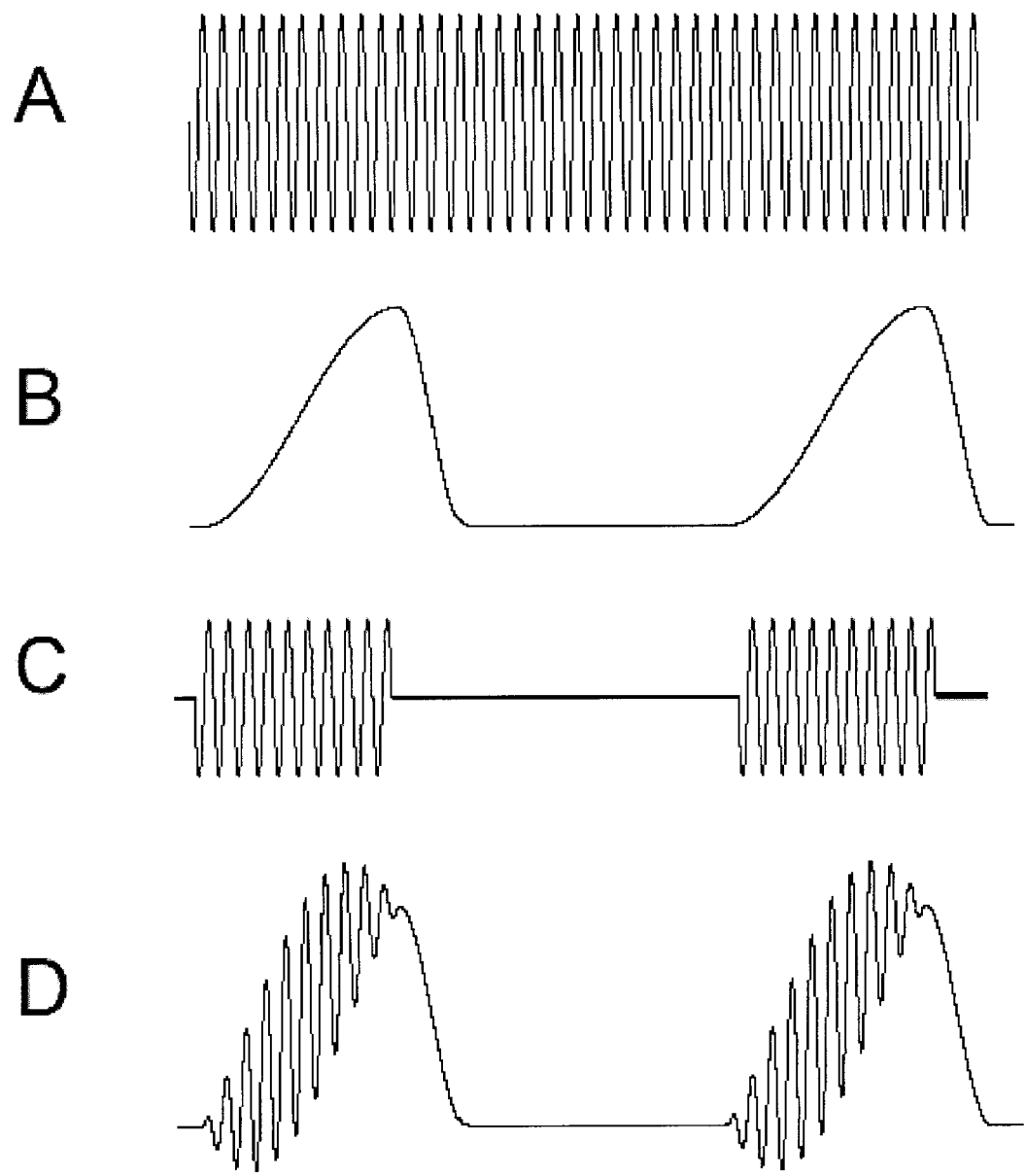
FIG. 9 illustrates another preferred embodiment of an axial displacement pattern for a phacoemulsification tip of the present invention.

Motion versus time plots in FIG. 3 depict typical prior art ultrasonic displacement patterns for phacoemulsification needles. FIG. 3A shows steady ultrasound displacement pattern. FIG. 3B shows a single burst of ultrasonic activity where 1 signals the attack portion, 2 signals the steady ultrasound portion and 3 signals the decay portion of the envelope of the single burst.

FIG. 3C shows a train of two independent bursts of ultrasonic activity separated by a resting period. These prior art motion patterns can be reproduced by activation of ultrasonic electro-mechanic transducer 60 of the present invention alone.

A motion versus time plot is depicted in FIG. 4C that shows the resultant axial motion pattern obtained by activation of ultrasonic electro-mechanic transducer 60 (FIG. 4A) using amplitude modulation (FIG. 4B). The motion pattern depicted in FIG. 4C is obtained after active cancellation of the ultrasonic electro-mechanic transducer 60 activity during the expected decreasing portion of the ultrasonic motion pattern thus avoiding to deliver ultrasonic energy during the inefficient portion of decreasing ultrasound amplitude.

A motion versus time plot is depicted in FIG. 5C that shows the resultant axial motion pattern obtained by simultaneous activation of ultrasonic electro-mechanic transducer 60 (FIG. 5A) and of low frequency electro-mechanic transducer 50 (FIG. 5B). The motion pattern depicted in FIG. 5C converts the steady ultrasound motion pattern into a progressive distal displacement motion pattern during the distal displacing phase of the low frequency component with increased efficiency. Contrarily, during the proximal displacing phase of the low frequency component, the steady ultrasound motion pattern is converted into a decreasing distal displacement motion pattern with reduced efficiency.

One embodiment of a motion versus time pattern of the present invention is depicted in FIG. 6D that shows the resultant axial motion pattern of the phacoemulsification needle tip obtained by activation of ultrasonic electro-mechanic transducer 60 (FIG. 6A) only during a selected portion (FIG. 6C) of the displacement cycle of the sinusoidal low frequency component according to the phase detector 32 output signal. Selective activation of ultrasonic electro-mechanic transducer 60 is preferably set to occur during the distally displacing phase of the low frequency electro-mechanic transducer 50 (FIG. 6B) for increased efficiency. Contrarily, during the proximally displacing phase of the low frequency electro-mechanic transducer 50 component, ultrasonic electro-mechanic transducer 60 is turned off as this is a reduced efficiency segment of the needle tip motion pattern.

Other embodiment of a motion versus time pattern of the present invention is depicted in FIG. 7D that shows the resultant axial motion pattern of the phacoemulsification needle tip obtained by activation of ultrasonic electro-mechanic transducer 60 (FIG. 7A) only during a selected portion (FIG. 7C) of the displacement cycle of the low frequency component according to the phase detector 32 output signal. Selective activation of ultrasonic electro-mechanic transducer 60 is preferably set to occur during the distally displacing phase of the low frequency electro-mechanic transducer 50 displacing phase for increased efficiency.

Contrarily, during the proximally displacing phase of the low frequency electro-mechanic transducer 50 component, ultrasonic electro-mechanic transducer 60 is turned off as this is a reduced efficiency segment of the needle tip motion pattern. This embodiment considers deviation of the low frequency displacement pattern from a sinusoidal waveform into an asymmetric waveform (FIG. 7B) where the distally displacing phase of the low frequency electro-mechanic transducer 50 motion cycles occurs slower than the proximally displacing phase.

Other embodiment of a motion versus time pattern of the present invention is depicted in FIG. 8D that shows the resultant axial motion pattern of the phacoemulsification needle tip obtained by activation of ultrasonic electro-mechanic transducer 60 (FIG. 8A) only during a selected portion (FIG. 8C) of the displacement cycle of the low frequency component according to the phase detector 32 output signal. Selective activation of ultrasonic electro-mechanic transducer 60 is preferably set to occur during the distally displacing phase of the low frequency electro-mechanic transducer 50 displacing phase for increased efficiency.

Contrarily, during the proximally displacing phase of the low frequency electro-mechanic transducer 50 component, ultrasonic electro-mechanic transducer 60 is turned off as this is a reduced efficiency segment of the needle tip motion pattern. This embodiment considers deviation of the low frequency displacement pattern from a sinusoidal waveform into an asymmetric waveform (FIG. 8B) where the distally displacing phase of the low frequency electro-mechanic transducer 50 motion cycles occurs faster than the proximally displacing phase.

Other embodiment of a motion versus time pattern of the present invention is depicted in FIG. 9D that shows the resultant axial motion pattern of the phacoemulsification needle tip obtained by activation of ultrasonic electro-mechanic transducer 60 (FIG. 9A) only during a selected portion (FIG. 9C) of the displacement cycle of the low frequency component according to the phase detector 32 output signal. Selective activation of ultrasonic electro-mechanic transducer 60 is preferably set to occur during the distally displacing phase of the low frequency electro-mechanic transducer 50 displacing phase for increased efficiency.

Contrarily, during the proximally displacing phase of the low frequency electro-mechanic transducer 50 component, ultrasonic electro-mechanic transducer 60 is turned off as this is a reduced efficiency segment of the needle tip motion pattern. This embodiment considers an inactivity period of the low frequency displacement component constituting repeated pulses of low frequency displacement activity (FIG. 9B).

Conclusions, ramifications and scope: While the above description contains many specificities these should not be construed as limitations on the scope of the invention, but rather as an exemplification of preferred embodiments thereof. Many other variations are possible. For example the low frequency carrier motion pattern may conform to other waveforms such as saw-tooth, inverted saw-tooth, triangle, etc.

The ultrasonic motion pattern may conform to other waveforms such as saw-tooth, inverted saw-tooth, triangle, etc. The ultrasonic component and the low frequency component of the motion waveform can be generated by activation of a single electro-mechanic actuator and driver.

The low frequency oscillator and the ultrasonic oscillator circuits can be an integral part of the hand-piece controller unit. The low frequency phase detector signal can be processed at hand-piece controller unit level or alternatively at ultrasonic oscillator—driver unit. The location and duration of the fraction of the low frequency motion cycle where ultrasonic bursts will take place may vary to maximize efficiency.

Accordingly, the scope of the present invention should be determined not by the embodiments illustrated but by the appended claims and their legal equivalents.

What is claimed is:

1. A method to improve the efficiency of a phacoemulsification system by delivering a burst of ultrasonic power synchronized with a fraction of a low frequency motion waveform at a phacoemulsification needle tip, the method comprising:

selecting an ultrasonic electro-mechanic actuator to axially oscillate a phacoemulsifier needle at ultrasonic frequency;

selecting a low frequency electro-mechanic actuator to axially oscillate a phacoemulsifier needle at low frequency;

mechanically combining the ultrasonic electro-mechanic actuator and the low frequency electro-mechanic actuator to obtain an axial phacoemulsification needle displacement pattern corresponding to the combined action of both ultrasonic and low frequency electro-mechanic actuators;

selecting a low frequency driver signal waveform to oscillate the low frequency electro-mechanic actuator;

selecting an ultrasonic driver signal waveform to oscillate the ultrasonic electro-mechanic actuator;

detecting a phase and position signal of the low frequency electro-mechanic actuator to synchronize bursts of ultrasonic actuator activity;

in a way that bursts of axial ultrasonic activity of the phacoemulsifier needle are repeatedly produced in synchronization with a fraction of each low frequency electro-mechanic actuator cycle.

* * * * *